(12) United States Patent
Hyslop et al.

(10) Patent No.: US 6,596,474 B1
(45) Date of Patent: Jul. 22, 2003

(54) PREVENTION AND TREATMENT OF AMYLOID-ASSOCIATED DISORDERS

(75) Inventors: Paul Andrew Hyslop, Indianapolis, IN (US); Foy Dean Miller, Camby, IN (US); Linda S. Higgins, Palo Alto, CA (US); Rosanne Catalano, Hayward, CA (US); Barbara Cordell, Palo Alto, CA (US); Elizbieta Puchacz, Pleasanton, CA (US)

(73) Assignees: Scios Inc., Sunnyvale, CA (US); Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/608,640

(22) Filed: Jun. 30, 2000

Related U.S. Application Data

(60) Provisional application No. 60/142,175, filed on Jul. 1, 1999.

(51) Int. Cl.⁷ ............... C12Q 1/00; C12P 21/04; C12N 5/06; C12N 5/00; A61K 35/55
(52) U.S. Cl. ............... 435/4; 435/70.3; 435/347; 435/374; 424/562
(58) Field of Search ............... 424/562; 435/4, 435/70.3, 373, 347

(56) References Cited

U.S. PATENT DOCUMENTS

| | | |
|---|---|---|
| 4,863,907 A | 9/1989 | Sakurai et al. |
| 5,236,910 A | 8/1993 | Egidio et al. |
| 5,264,425 A | 11/1993 | Dal Pozzo et al. |
| 5,302,386 A | 4/1994 | Kasper et al. |
| 5,318,890 A | 6/1994 | Rosen et al. |
| 5,403,919 A | 4/1995 | Butcher |
| 5,580,748 A | 12/1996 | Alkon et al. |
| 5,763,504 A | 6/1998 | Matsuda et al. |
| 6,043,224 A | 3/2000 | Lee et al. |
| 6,107,050 A | 8/2000 | Alkon et al. |

FOREIGN PATENT DOCUMENTS

| | | |
|---|---|---|
| CA | 2131754 | 9/1994 |

OTHER PUBLICATIONS

Woodroofe, M.N. Cytokine expression by microglia in vitro and in the central nervous system in multiple sclerosis. J.Physiology, 1996, 493.P, 45S.*
Yambe T. et al. Cytokine–gene expression in measles–infected adult human glial cells. J.Neuroimmunology, 1994, 49, pp. 171–179.*
Yoshioka M. et al. The release of tumor necrosis factor–alpha, interleukin–1, interleukin–6 and prostaglandin E2 in bovine Kupffer cells stimulated with bacterial lipopolysaccharide. Veterinary Immunology and Immunopathology, 1998, 66, pp. 301–307.*
Ganter et al., 1992, J. Neurosci. Res.., 33, pp. 218–230.*
Fiebich et al. (1998), "Potential Link Between Interleukin–6 and Arachidonic Acid Metabolism in Alzheimer's Disease." *J. Neural. Transm.*, vol. 54:269–278.
Fiebach et al., GLIA, (Oct. 1996) 18(2):152–60.

* cited by examiner

*Primary Examiner*—John Ulm
*Assistant Examiner*—Olga N. Chernyshev
(74) *Attorney, Agent, or Firm*—Karl Bozicevic; Bozicevic, Field & Francis LLP

(57) ABSTRACT

The present invention provides assays to identify compounds that affect microglial cell activation, and specifically assays to identify compounds that affect secretion of cytokines from these microglial cells by modulating $PGE_2$-mediated activity. The assays of the invention include assays for testing microglial cell activation by contacting microglia with compounds that modulate β-amyloid $PGE_2$-mediated activation, which can be identified by cellular activity such as secretion of cytokines, e.g., TNF-α and IL-1α. The effect of the candidate compound can be determined by comparing the effect with a control culture which is not contacted with the compound, or by comparing the effect with a standardized profile.

11 Claims, 8 Drawing Sheets

SEQUENCE LISTING

<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: primer

<400> SEQUENCE: 1
gcagcgagct ggcctcccag g          21

<210> SEQ ID NO 2
<211> LENGTH: 23
<212> TYPE: DNA
<213> ORGANISM: Artificial Sequence
<220> FEATURE:
<223> OTHER INFORMATION: primer

<400> SEQUENCE: 2
ccagcttgtc ggtatcatgg tgg          23

<210> SEQ ID NO 3
<211> LENGTH: 22
<212> TYPE: DNA
<213> ORGANISM: Artificial Sequence
<220> FEATURE:
<223> OTHER INFORMATION: primer

<400> SEQUENCE: 3
gttgcatctt gtgttcttaa tg          22

```
<210> SEQ ID NO 4
<211> LENGTH: 23
<212> TYPE: DNA
<213> ORGANISM: Artificial Sequence
<220> FEATURE:
<223> OTHER INFORMATION: primer

<400> SEQUENCE: 4
gcttctcatt gtctcggtgc tcg                                              23

<210> SEQ ID NO 5
<211> LENGTH: 23
<212> TYPE: DNA
<213> ORGANISM: Artificial Sequence
<220> FEATURE:
<223> OTHER INFORMATION: primer

<400> SEQUENCE: 5
caactgatgt ctgattgaag atc                                              23

<210> SEQ ID NO 6
<211> LENGTH: 23
<212> TYPE: DNA
<213> ORGANISM: Artificial Sequence
<220> FEATURE:
<223> OTHER INFORMATION: primer

<400> SEQUENCE: 6
ggagaccagc agaccgacag cac                                              23

<210> SEQ ID NO 7
<211> LENGTH: 21
<212> TYPE: DNA
<213> ORGANISM: Artificial Sequence
<220> FEATURE:
<223> OTHER INFORMATION: primer

<400> SEQUENCE: 7
gcaatagaga agatcaaatg c                                                21

<210> SEQ ID NO 8
<211> LENGTH: 21
<212> TYPE: DNA
<213> ORGANISM: Artificial Sequence
<220> FEATURE:
<223> OTHER INFORMATION: primer

<400> SEQUENCE: 8
ctgataagtt cagtgtttca c                                                21
```

PREVENTION AND TREATMENT OF AMYLOID-ASSOCIATED DISORDERS

CROSS-REFERENCE

This application claims priority to U.S. provisional application Ser. No. 60/142,175, filed Jul. 1, 1999, which application is incorporated herein by reference in its entirety.

FIELD OF THE INVENTION

The invention relates generally to the treatment of neurological diseases and specifically to treatment of neurological diseases involving amyloid plaque formation.

BACKGROUND OF THE INVENTION

A number of important neurological diseases including Alzheimer's disease (AD), cerebral amyloid angiopathy (CAA), and prion-mediated diseases are characterized by the deposition of aggregated proteins, referred to as amyloid, in the central nervous system (CNS) (for reviews, see Glenner et al. (1989) *J. Neurol. Sci.* 94:1–28; Haan et al. (1990) *Clin. Neurol. Neurosurg.* 92(4):305–310. These highly insoluble aggregates are composed of nonbranching, fibrillar proteins with the common characteristic of a β-pleated sheet conformation. In the CNS, amyloid can be present in cerebral and meningeal blood vessels (cerebrovascular deposits) and in brain parenchyma (plaques). Neuropathological studies in human and animal models indicate that cells proximal to amyloid deposits are disturbed in their normal functions (Mandybur (1989) *Acta Neuropathol.* 78:329–331; Kawai et al. (1993) *Brain Res.* 623:142–6; Martin et al. (1994) *Am. J. Pathol.* 145:1348–1381; Kalaria et al. (1995) Neuroreport 6:477–80; Masliah et al. (1996) *J. Neurosci.* 16:5795–5811). AD studies additionally indicate that amyloid fibrils may actually initiate neurodegeneration (Lendon et al. (1997) *J. Am. Med. Assoc.* 277:825–31; Yankner (1996) *Nat. Med.* 2:850–2; Selkoe (1996) *J. Biol. Chem.* 271:18295–8; Hardy (1997) *Trends Neurosci.* 20:154–9).

AD and CAA share biochemical and neuropathological markers, but differ somewhat in the extent and location of amyloid deposits as well as in the symptoms exhibited by affected individuals. The neurodegenerative process of AD, the most common cause of progressive intellectual failure in aged humans, is characterized by the progressive and irreversible deafferentation of the limbic system, association neocortex, and basal forebrain accompanied by neuritic plaque and tangle formation (for a review see Terry et al. (1994) "Structural alteration in Alzheimer's disease." In: Alzheimer's disease (Terry et al. eds.), pp. 179–196. Raven Press, New York). Dystrophic neurites, as well as reactive astrocytes and microglia, are associated with these amyloid-associated neurite plaques. Although, the neuritic population in any given plaque is mixed, the plaques generally are composed of spherical neurites that contain synaptic proteins, APP (type I), and fusiform neurites containing cytoskeletal proteins and paired helical filaments (PHF; type II).

CAA patients display various vascular syndromes, of which the most documented is cerebral parenchymal hemorrhage. Cerebral parenchymal hemorrhage is the result of extensive amyloid deposition within cerebral vessels (Hardy (1997) *Trends Neurosci.* 20:154–9; Haan et al. (1990) *Clin. Neurol. Neurosurg.* 92:305–10; Terry et al., supra; Vinters (1987) *Stroke* 18:211–24; Itoh et al. (1993) *J. Neurological Sci.* 116:135–41; Yamada et al. (1993) *J. Neurol. Neurosurg. Psychiatry* 56:543–7; Greenberg et al. (1993) *Neurology* 43:2073–9; Levy et al. (1990) Science 2481124–6). In some familial CAA cases, dementia was noted before the onset of hemorrhages, suggesting the possibility that cerebrovascular amyloid deposits may also interfere with cognitive functions.

The precise mechanisms by which neuritic plaques are formed and the relationship of plaque formation to the AD-associated and CAA-associated neurodegenerative processes are not well-defined. Several factors that increase the likelihood of developing AD have already been identified. The risk of developing AD definitely increases with: (1) age, (2) head injuries, (3) family history of AD or Down syndrome, (4) sex, with a higher prevalence of AD in women, (5) vascular disease, (6) exposure to environmental toxins, (7) infectious processes, or (8) changes in immune function. Recent advances in molecular genetics have suggested that genetic predisposition is one of the most important risk factors in the development of AD. For example, a significant increase in the number of amyloid plaques in AD patients with an apolipoprotein E4 (apoE4) allele has been observed and the results of several genetic studies indicate that the etiology of this neurodegenerative disease is associated with the presence of the apoE4 allele.

In both AD and CAA, the main amyloid component is the amyloid β protein (Aβ). The Aβ peptide, which is generated from the amyloid β precursor protein (APP) by two putative secretases, is present at low levels in the normal CNS and blood. Two major variants, $A\beta_{1-40}$ and $A\beta_{1-42}$, are produced by alternative carboxy-terminal truncation of APP (Selkoe et al.(1988) *Proc. Natl. Acad. Sci.* USA 85:7341–7345; Selkoe, (1993) *Trends Neurosci* 16:403–409). $A\beta_{1-42}$ is the more fibrillogenic and more abundant of the two peptides in amyloid deposits of both AD and CAA. In addition to the amyloid deposits in AD cases described above, most AD cases are also associated with amyloid deposition in the vascular walls (Hardy (1997), supra; Haan et al. (1990), supra; Terry et al., supra; Vinters (1987), supra; Itoh et al. (1993), supra; Yamada et al. (1993), supra; Greenberg et al. (1993), supra; Levy et al. (1990), supra). These vascular lesions are the hallmark of CAA, which can exist in the absence of AD.

Glial cell activation is believed to play an essential pathogenic role in the development of dementia. A source of damage in the AD brain is an altered response triggered by microglial activation, which is associated with amyloid plaques. For example, a correlation between genetic predisposition and the proliferation and activation of microglial cells was obtained in AD primary in vitro microglial cell cultures (Lombardi et al. (1998) *J Neurosci Res* 54:539–53). Many studies have shown that microglia secrete both cytokines and cytotoxins and since reactive microglia appears in nearly every type of brain damage, it is likely that their secreted products ultimately help to determine the rate of damaged brain tissue. See e.g., Giulian, et al. (1994) *Neurochem Int.* 25:227–33. Reactive microglia may also contribute to neuronal damage by the generation of free oxygen radicals and nitric oxide (NO), which forms the particularly aggressive peroxynitrites, and by the release of potentially neurotoxic cytokines such as tumor necrosis factor-α (TNF-α) (P. Schubert et al. (1998) *Alzheimer Dis Assoc Disord.*, 12 Suppl 2:S21–8).

Prostaglandins and nitric oxide (NO) are among the numerous substances released by activated microglial cells. Cyclooxygenase-2 (COX-2) and inducible NO synthase (iNOS), the two key enzymes in prostaglandin and NO synthesis, respectively, are rapidly co-induced in rat neonatal microglial cultures activated by bacterial endotoxin (lipopolysaccharide [LPS]). COX-2 expression appears to be under the negative control of endogenous as well as exogenous NO (Minghetti et al. (1997) *Eur J Neurosci.* 9:934–40). Inhibitors of the inducible form of cyclooxygenase (COX-2) have been examined for the treatment of AD. It is becoming increasingly clear, however, that the products of COX-2 mediate both pro- and anti-inflammatory responses, and that inhibiting all COX-2 products in chronic neuroinflammatory states to reduce neuroinflammation inhibits the anti-inflammatory properties certain COX-2 products. Caggiano, (1998) *J. Neurochemistry* 70:2357–68. For example, $PGI_2$ and $PGF_{2\alpha}$ are associated with anti-inflammatory activity, and regulation using COX-2 inhibitors may reduce their anti-inflammatory effects.

Prostaglandin E2 ($PGE_2$) is also produced by activated microglial cells, and is known to increase cyclic adenosine monophosphate (cAMP) levels in microglial cells (Minghetti et al., supra). Traditionally, $PGE_2$ has been considered to be a positive factor in inflammation. More recently, however, $PGE_2$ has been shown to: 1) protect neurons from cytotoxic injury (Akaike et al. (1994) *Brain Research*, 663:237–243); 2) inhibit LPS-induced outwardly rectifying potassium current and IL-1β production (Caggiano et al., (1998) *J. Neurochemistry*, 70:2357–68); 3) downregulate LPS-induced iNOS expression in a dose-dependent manner in cultured rat microglia (Minghetti (1997) *Glia*, 19:152–60); and 4) reduce nitrous oxide-mediated cell injury by microglia (Thery, (1994) *Glia*, 11:383–86). In addition, $PGE_2$ has been shown to modulate macrophage-derived TNF-α gene expression (S. L. Kunkle et al. (1998) *J. Biol. Chem*, 263:5380–84).

There is a need in the art for a more specific therapeutic targeting system to control microglial cell activation. In addition, there is a need for a method of inhibiting amyloid plaque formation in patients suffering from neurodegenerative disorders.

SUMMARY OF THE INVENTION

The present invention provides assays to identify compounds that affect microglial cell activation, compounds identified in these assays which inhibit Aβ:$PGE_2$ activation of microglial cells, and methods of using such compounds in therapeutic intervention. Assays of the invention affect microglia activation through modulation of Aβ:$PGE_2$-mediated activity. Aβ:$PGE_2$ exposure to microglia activates the microglia to a greater extent than additive exposure to either agent alone. Since this synergistic activation of microglia presents a particularly pathogenic mechanism, methods of identifying compounds using the assays of the invention are particularly useful, since they can identify therapeutic agents that inhibit either or both arms of the synergistic effect. Moreover, the therapeutic agents identified using the assays of the invention may be particularly suited for patient intervention, as they exhibit a specific effect on this synergistic activation process.

The assays of the invention include assays for testing microglial cell activation by contacting microglia with compounds that modulate Aβ and/or $PGE_2$-mediated activation. The effect of the candidate compound can be determined by comparing the effect with a control culture which is not in contact with the compound, for example by measuring secretion of cytokines such as TNF-α and IL-1α or by comparing the effect with a standardized cytokine profile.

In one preferred embodiment, the invention features an assay to identify compounds which alter, halt or prevent progression of an amyloid-associated disorder by culturing microglial cells with Aβ:$PGE_2$ and a compound to be tested. The culture is then examined for synergistic activation by Aβ:$PGE_2$ as evidence by a change in cellular activity, for example cytokine secretion, elevation of nitric oxide synthetase (NOS) or its products, reactive oxygen species (ROS) or expression of molecules associated with activation such as LFA-1, VLA-4, or Mac-1. The culture can also be compared to levels prior to exposure with the compound or, alternatively, to a standardized profile for one or more of these cellular activities. The compound may be added to the cells prior to exposure with the Aβ peptide (e.g., to examine the ability of the compound to prevent plaque formation), simultaneously with the Aβ peptide, or following incubation with the Aβ peptide (e.g., to determine the ability of the compound to halt or reverse progression of plaque formation). Preferably, the amyloid-associated disorder is AD or CAA, and the cytokine used in the assay is preferably IL-1α, IL-1β, TNF-α and/or IL-6.

The invention also features a method for determining the particular molecules that are therapeutic targets for modulation of microglia activation. For example, the receptor isoform involved in the Aβ:$PGE_2$ synergy was determined by using compounds that affects a particular isoform of $PGE_2$, and the receptor isoform involved was identified by examining the effect of the compounds on microglia activation.

In another embodiment, the invention provides a method for modulating cytokine secretion in a patient by analyzing microglial cells from the central nervous system of a patient, determining the level of expression of cytokines from the microglial cells, and administering a compound in an amount sufficient to reduce cytokine expression. Cytokine secretion may be monitored, e.g., by monitoring soluble factors associated with microglial cell activation from the cerebrospinal fluid of a patient, which can be obtained via a spinal tap.

The invention also provides a method for reducing the level of β-amyloid plaque in the brain tissue of a mammalian host by administering to the host a compound in an amount effective to reduce microglial activation. Preferably, the compound used in treatment reduces the microglial activation by 30 to 80%, and reduces cytokine secretion levels by 20 to 80%.

The invention also provides standardized cellular profiles and methods of using such standards as a positive control in a neurodegenerative disease assay. The assay may be a bioassay which uses transgenic animals or an immunoassay, and can be used for purposes such as diagnosis, prognosis, determination of the efficacy of a therapeutic, etc. The standards function to ensure reproducibility and specificity of an assay by functioning as a reference material with a known and consistent level of microglial activation. The standards also make it possible to determine sensitivity and to adjust selectivity relative to sensitivity as needed.

The invention also features a method of calibrating an assay using the standards of the invention. Calibration can be within a single assay, to determine efficacy at a given level of cytokine concentration, or between assays, to allow comparison of results of different assays by adjusting detection levels between assays. For example, if one assay is more sensitive than another, calibration with a standard can be used to determine the factor for converting measured levels to corrected levels for comparison of results obtained using different assays.

The invention also features a method of determining the quality of reagents used in a diagnostic or prognostic assay by testing the reagents using standards of the invention. The standards provide a consistent level of microglial activation, and preferably a consistent background. Testing reagents against the standard can ensure selectivity and/or reproducibility of a reagent used in an assay.

An object of the invention is to identify therapeutic compounds that reduce amyloid plaque burden by regulating a $PGE_2$-mediated pathway.

Another object of the invention is to use the synergistic effects of the Aβ peptide and certain cytokines to identify therapeutic agents for amyloid-associated disorders.

Another object of the invention is to identify the specific molecules involved in neurodegenerative disorders by using compounds targeted to specific molecules involved in microglia activation.

Another object of the invention is to treat patients with a neurodegenerative disorder by administering a compound identified using the assays of the invention.

Another object of the invention is to prevent amyloid plaque formation by administering a compound identified using the assays of the invention.

An advantage of the invention is that the assays of the invention can identify therapeutic agents that target a specific pathway, and thus have fewer general side effects.

Another advantage of the invention is that it provides more narrowly tailored therapeutic agents. In particular, since human microglia do not express EP3, therapeutics can be used that do not have side effects associated with targeting EP3.

These and other objects, advantages and features of the invention will become apparent to those skilled in the art upon reading this disclosure.

DETAILED DESCRIPTION OF PREFERRED EMBODIMENTS

Figure 1:
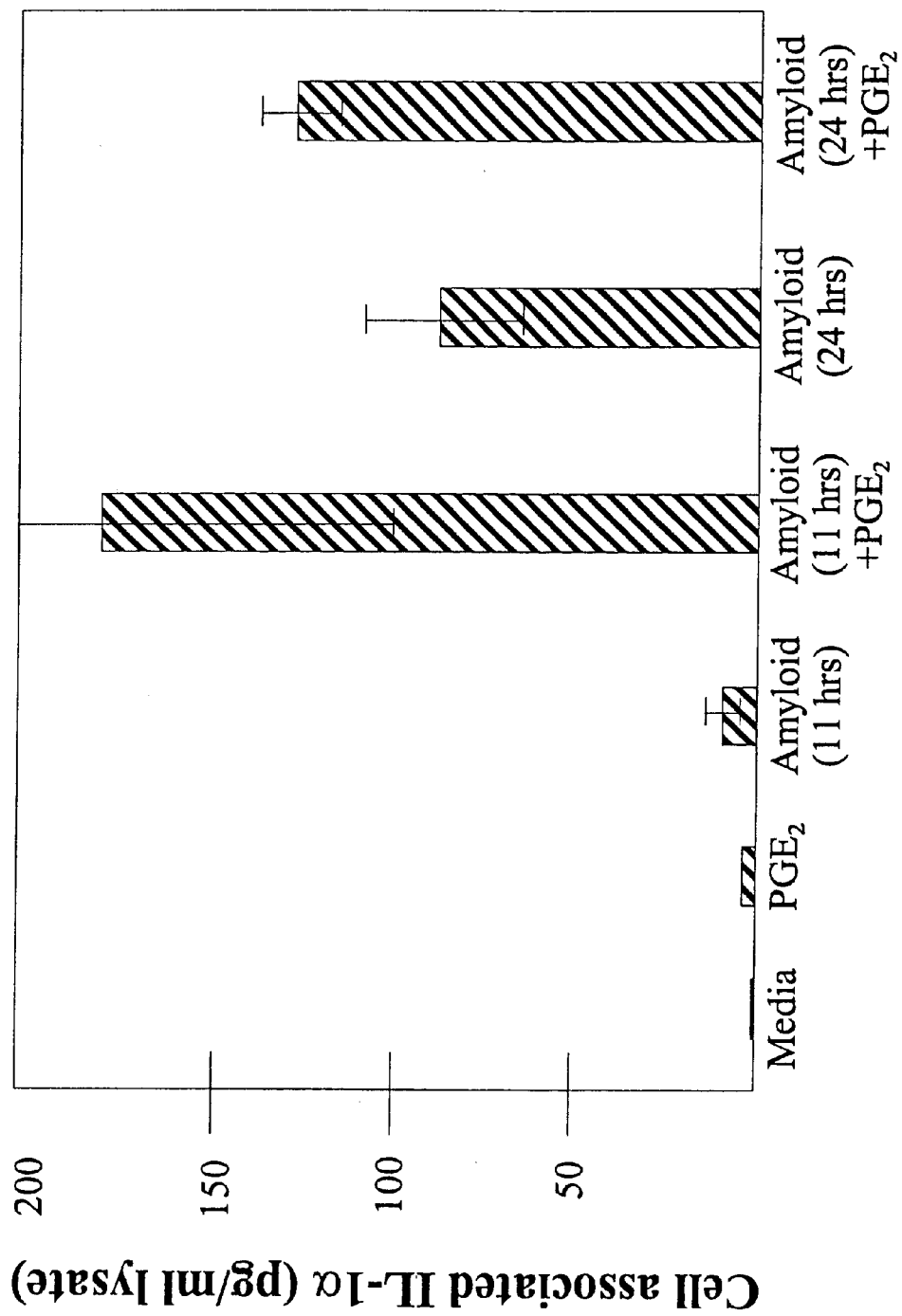
FIG. 1 is a bar graph illustrating the $PGE_2$:Aβ synergy in primary cortical mixed glial cells as evidenced by change in levels of intracellular IL-1α levels.

Before the present methods and compounds are described, it is to be understood that this invention is not limited to particular methods or compounds described and may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an," and "the" include plural referents unless the context clearly dictates otherwise. Thus, for example, reference to "a compound" includes a plurality of such compounds and reference to "an AD-type pathology" includes reference to one or more such pathologies and equivalents thereof known to those skilled in the art, and so forth.

All publications mentioned herein are incorporated herein by reference for the purpose of =describing and disclosing, for example, the cell lines, constructs, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention. Further, the publication dates provided may be different from the actual publication date which may require independent verification.

DEFINITIONS

The terms "treatment", "treating", "treat" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, particularly a human, and includes:

(a) preventing the disease or symptom from occurring in a subject which may be predisposed to the disease or symptom but has not yet been diagnosed as having it;

(b) inhibiting the disease symptom, i.e., arresting its development; or (c) relieving the disease symptom, i.e., causing regression of the disease or symptom.

By "effective dose" or "amount effective" is meant an administration of a compound sufficient to provide the desired physiological and/or psychological change. This will vary depending on the patient, the disease and the treatment. The dose may either be a therapeutic dose, in which case it should sufficiently alter levels of amyloid plaques in the subject to alleviate or ameliorate the symptoms of the disorder or condition, or a prophylactic dose, which should be sufficient to prevent accumulation of amyloid plaques to an undesirable level.

The term "compound" as used herein describes any molecule, e.g., protein or small molecule pharmaceutical, with the capability of affecting the molecular and clinical phenomena associated with amyloid-associated disorders, and specifically AD- and/or CAA-mediated disorders.

The term "diagnosis" is used herein to cover any type of analysis used to determine or project a status which includes identification of a disease from its symptoms and determining the presence of molecules (e.g., TGF-α or IL-1α) in an area (e.g., brain tissue) which suggest a disease status (e.g., beginnings of Alzheimer's disease).

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The term "Alzheimer's disease" (abbreviated herein as "AD") as used herein refers to a condition associated with formation of neuritic plaques comprised primarily of β-amyloid protein primarily in the hippocampus and cerebral cortex, as well as impairment in both learning and memory. "AD" as used herein is meant to encompass both AD as well as AD-type pathologies.

The term "AD-type pathology" as used herein refers to a combination of CNS alterations including, but not limited to, formation of neuritic plaques containing β-amyloid protein in the hippocampus and cerebral cortex. Such AD-type pathologies can include, but are not necessarily limited to, disorders associated with aberrant expression and/or deposition of APP, overexpression of APP, expression of aberrant APP gene products, and other phenomena associated with AD. Exemplary AD-type pathologies include, but are not necessarily limited to, AD-type pathologies associated with Down's syndrome that is associated with overexpression of APP.

The term "phenomenon associated with Alzheimer's disease" as used herein refers to a structural, molecular, or functional event associated with AD, particularly such an event that is readily assessable in an animal model. Such events include, but are not limited to, amyloid deposition, neuropathological developments, learning and memory deficits, and other AD- associated characteristics.

The term "cerebral amyloid angiopathy" (abbreviated herein as CAA) as used herein refers to a condition associated with formation of amyloid deposition within cerebral vessels which can be complicated by cerebral parenchymal hemorrhage. CAA is associated with increased risk of stroke as well as development of cerebellar and subarachnoid hemorrhages Vinters (1987) *Stroke* 18:311–324; Haan et al. (1994) *Dementia* 5:210–213; Itoh et al. (1993) *Neurol. Sci.* 116:135–414). CAA can also be associated with dementia prior to onset of hemorrhages. The vascular amyloid deposits associated with CAA can exist in the absence of AD, but are more frequently associated with AD.

The term "phenomenon associated with cerebral amyloid angiopathy" as used herein refers to a molecular, structural, or functional event associated with CAA, particularly such an event that is readily assessable in an animal model. Such events include, but are not limited to, amyloid deposition, cerebral parenchymal hemorrhage, and other CAA-associated characteristics.

The term "β-amyloid deposit" as used herein refers to a deposit in the brain composed of Aβ as well as other substances.

The term "synergy" as used herein refers to a response to two or more stimuli that is greater than the sum of the response of the same stimuli applied alone. For example, microglial cells exposed to Aβ:PGE$_2$ exhibit a greater level than the sum of activation than either Aβ or PGE$_2$ alone, as evidenced for example by cytokine elevation. Similarly, a "synergistic effect" is an effect result from a synergy, e.g., increased expression of cytokines in response to Aβ:PGE$_2$ activation of microglial cells.

The term "a standardized profile", "standard" and the like as used herein refer to a preparation for microglial cell activation assays in which the level of a cellular activity, e.g., cytokine expression, and background characteristics are sufficiently established to allow the standard to function as a reference material, e.g., for immunoassays and/or bioassays. The standardized profiles have one or more properties sufficiently well established to be used to determine microglial activation. Such properties are preferably a change in cellular activity, for example cytokine secretion, elevation of nitric oxide synthetase (NOS) or its products, reactive oxygen species (ROS) or expression of molecules associated with activation such as LFA-1, VLA-4, or Mac-1.

GENERAL METHODOLOGY

The assays, methods, and compounds of the present invention are directed to the use of PGE$_2$ receptors on microglia as therapeutic targets to modulate microglial, activation, and in particular to control microglial secretion, e.g., cytokine release. A central finding upon which the present invention is based is that PGE$_2$ receptor isoforms EP2 and EP4 are present on microglia. The assays and methods of the present invention are based on the observations of: 1) a synergistic response between a PGE$_2$ isoform and Aβ in microglial activation, as evidenced by the induction of a second inflammatory mediator, TNF-α; and 2) synergistic responses between a PGE$_2$ isoform and Aβ in primary glial cell cultures as evidenced by IL-1α synthesis/secretion. These IL-1α responses may be used to identify the molecules involved in particular neurodegenerative diseases, and to identify compounds which alter, halt or prevent progression of these diseases by manipulation of PGE$_2$ receptor isoform activity and/or activity of other molecules in the PGE$_2$ signaling pathway. Compounds identified as controlling activity through a PGE$_2$ receptor isoform can be used to alter microglial activation and protein secretion, thus altering the progression of inflammatory response in neurodegenerative disorders.

For example, the assays of the invention were used to identify the particular PGE$_2$ receptor isoform involved in microglial activation in response to Aβ. The finding that the EP4 isoform of the PGE$_2$ receptor is involved in microglia activation allows therapeutic targeting of EP4 to control synergistic PGE$_2$:Aβ microglial activation with compounds that are specific to the EP4 isoform, but that do not affect the other PGE$_2$ isoforms. This is a major advantage over traditional NSAIDs and COX-2 inhibitors, effects of which include effects of other isoforms including EP3, since EP3 is known to mediate gastrointestinal disturbance including stomach bleeding and induction of ulcers. Compounds identified by the methods of the invention can be used to block the deleterious effect of PGE$_2$ in microglia while preserving the positive effects of PGE$_2$ in areas such as the gut.

EXEMPLARY ASSAYS OF THE INVENTION

To identify and characterize compounds which modulate Aβ:PGE$_2$-mediated microglial activation, both in vivo or in vitro methods can be used. The test samples that may be used in the various in vitro assays include, but are not limited to, an aliquot of tissue culture medium conditioned by murine cultured cells, an aliquot of tissue culture medium conditioned by human cultured cells, murine cultured cell extract, tissue culture medium conditioned by mouse brain organotypic slice or explant, murine organotypic brain slice or explant extract, human cultured cell extract, mouse plasma, human plasma, plasma from transgenic mice genetically engineered to express any one of the three human apoE isoforms, plasma from transgenic mice having an altered APP, or human or mouse CSF or tissue extract.

In vitro Assays

Various in vitro assays can be used to measure effects of the inventive compounds to alter Aβ and PGE$_2$-mediated microglial activation. The effect of compounds on Aβ and PGE$_2$-mediated microglial secretion can be measured by methods including, but not limited to, an enzyme-linked immuno-sorbent assay (ELISA), Western blot analysis, or immunoprecipitation of the cellular media, immunocytochemistry, Griess reaction, or assessment of ROS or NO.

For example, an in vitro assay may determine the effect of a compound on the synergistic response between $PGE_2$ and $A\beta$ by measuring levels of cytokine, and in particular TNF-$\alpha$, IL-1$\alpha$. or IL-6. Equivalent amounts of a microglial cell line or primary brain cultures including microglia are cultured in a 96-well microtiter plate. Cultures are treated with $A\beta$ and $PGE_2$. Varying doses of compounds (drug) are added to the cells to the microtiter plate, and the cells incubated for an appropriate period of time, e.g., 12 hours at 37° C. At the conclusion of the incubation, the levels of cytokine secreted into the cell media and lysates can be measured to determine the effect of the compound.

In yet another example, IL-1$\alpha$ or IL-6 responses may be used to identify the $PGE_2$ receptor isoforms involved in particular neurodegenerative diseases, and to identify compounds which alter, halt or prevent progression of these diseases by manipulation of $PGE_2$ activity. This is done by a direct assay on the cells themselves. Cells involved in a neurodgenerative pathological state, such as microglial cells, can be analyzed for the presence or absence of $PGE_2$ recptor isoform mRNA, and in particular the EP4 isoform, by RT-PCR analysis.

In yet another example, a mixed lymphocyte reaction (MLR) provides a valuable screening tool to determine biological activity of each inventive compound using PMBC as a surrogate marker for microglial activation. In the MLR, PBMCs (peripheral blood mononuclear cells) are obtained by drawing whole blood from healthy volunteers in a heparinized container and diluted with an equal volume of hanks balanced salt solution (HBSS). This mixture is layered on a sucrose density gradient, such as a FICOLL-HYPAQUE® gradient, and centrifuged at 1000× g for 25 minutes at room temperature or cooler. PBMC are obtained from a band at a plasma-Ficoll interface, separated and washed at least twice in a saline solution, such as HBSS. Contaminated red cells are lysed, such as by ACK lysis for 10 min at 37° C., and the PBMCs are washed twice in HBSS. The pellet of purified PBMCs is resuspended in complete medium, such as RPMI 1640 plus 20% human inactivated serum. PBMC activation and/or cytokine secretion is determined in an MLR performed in a 96-well microtiter plate. Briefly, approximately $10^5$ purified PBMC cells in 200 $\mu$l complete medium are co-cultured, and treated with $A\beta$ and $PGE_2$ either in the presence or absence of a candidate compound. The effect of the compound on microglial activation is then determined.

Other in vitro assays utilizing the methods of the invention may also be employed, and will be apparent to one skilled in the art upon reading this disclosure and the exemplary assays described herein.

Bioassays

Animal models for Alzheimer's disease may be used to determine the effect of compounds on $PGE_2$-mediated microglial activation. The screening for AD phenotype can include assessment of phenomena including, but not limited to: 1) analysis of molecular markers (e.g., levels of secretion of cytokines in brain tissue; presence/absence of $PGE_2$ activity, presence/absence in brain tissue of various A$\alpha$ activated glia, formation of neurite plaques, and the like); 2) assessment of behavioral symptoms associated with memory and learning; 3) detection of neurodegeneration characterized by loss of select populations of neurons (neurodegeneration can be measured by, for example, detection of synaptophysin expression in brain tissue or by direct quantitation based on morphology after staining with a neuronal cell body protein such as neurofilament) (see, e.g., Games et al. (1995) Nature 373:523–7). The screening for CAA can include assessment of phenomena including, but not limited to: 1) analysis of molecular markers (e.g., levels of expression of proteins in brain vascular tissue; presence/absence in brain tissue of various genetic variants, isoforms, and mutants associated with CAA; formation of cerebrovascular amyloid deposits); and 2) detection of cerebral hemorrhage associated with amyloid deposition. These phenomena may be assessed in the screening assays either singly or in any combination.

Preferably, the screen will include control values (e.g., the level of amyloid production in the test animal in the absence of test compound(s)). Test substances which are considered positive (i.e., likely to be beneficial in the treatment of AD or CAA) will be those which have a substantial effect upon an AD- or CAA-associated phenomenon e.g., test agents that are able to reduce the level of A$\alpha$ deposition, preferably by at least 20%, more preferably by at least 50%, and most preferably by at least 80%.

Methods for assessing these phenomena, and the effects expected of a compound for treatment of AD and/or CAA, are well known in the art. For example, methods for using transgenic animals in various screening assays for, for example, testing compounds for an effect on AD, are found in WO 96/40896, published Dec. 19, 1996; WO 96/40895, published Dec. 19, 1996; WO 95/11994, published May 4, 1995 (describing methods and compositions for in vivo monitoring of $A\beta$; each of which is incorporated herein by reference with respect to disclosure of methods and compositions for such screening assays and techniques).

After exposure to the compound, the animals are sacrificed and analyzed by immunohistology for either: 1) neuritic plaques in the brain (AD model) and/or 2) amyloid deposition on cerebrovascular walls (CAA model) and/or 3) microglial number and/or activation state (normal animal). The brain tissue is fixed (e.g, in 4% paraformladehyde) and sectioned; the sections are stained with antibodies reactive with expression of a sequence indicative of $PGE_2$-mediated microglial activation, such as TNF-$\alpha$, the $A\beta$ peptide, LFA-1, VLA-4, IL-6 or IL-1$\alpha$. Secondary antibodies conjugated with fluorescein, rhodamine, horse radish peroxidase, or alkaline phosphatase are used to detect the primary antibody. These experiments permit identification of amyloid plaques and the regionalization of these plaques to specific areas of the of brain.

Sections are also stained with other antibodies diagnostic of Alzheimer's plaques, recognizing antigens such as Alz-50, tau, A2B5, neurofilaments, neuron-specific enolase, and others that are characteristic of Alzheimer's and/or CAA plaques. Staining with thioflavins and congo red can also be carried out to analyze co-localization of $A\beta$ deposits within the neuritic plaques and NFTs of AD or along the vascular walls as in CAA.

Standardized Profiles

In another embodiment of the invention, $A\beta$:$PGE_2$-mediated microglial cell activation and/or cytokine production is determined using a standardized profile. This profile may be used to determine differences between cells treated with a compound, e.g., a $PGE_2$ receptor antagonist, and a standardized profile of untreated cells of that particular cell type. The standardized profiles are created using a statistically significant number of samples, preferably at least 20, more preferably at least 50, and even more preferably at least 100. When primary cultures are used for the standard, the samples used to produce the standard profiles are preferably matched for age, phenotype, etc. For example, a standardized profile can be determined for peripheral blood samples from 70–84 year-old persons affected with AD. In another example, a standardized profile can be determined for cells from 70–85 year-old non-demented persons. In yet another example, a standard may be determined for a microglial cell line.

Once a standard has been generated and the critical properties determined, this standard can be used to harmonize data between assays. For example, comparative microglial activation assays may vary in protocol, resulting in different assay values for a human sample. By performing each of these assays on the standard with known properties as a control, a correction value may be determined to allow harmonization between different assays. The human CNS standard is diluted into multiple concentrations, for example a 1:2 dilution, a 1:5 dilution, a 1:10 dilution and a 1:50 dilution, and the comparative microglial activation assay performed on each of the dilutions of the human sample. The results of the assay values retrieved for each dilution are used to determine a correction value to harmonize the data to reflect the determined true value of the microglial activation in the sample.

COMPOUNDS OF THE INVENTION

The assays of the invention can be used to identify compounds for use as therapeutics in the treatment of neurological disorders, e.g., AD or CAA. Compounds of the invention may affect any pathway involved in the synergistic activation of microglia, and preferably alter activity mediated by a $PGE_2$ receptor isoform, and in particular activity mediated by the EP4 isoform. Compounds identified as altering microglial activation using the methods of the invention can be used as therapeutic and/or prophylactic agents in the treatment of neurological disorders.

Candidate compounds can be obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological compounds may be subjected to directed or random chemical modifications, such as acylation, alkylation, esterification, amidification, etc. to produce structural analogs.

TREATMENT OF NEURODEGENERATIVE DISORDERS

Compounds identified using the methods and assays of the invention may be administered to a subject in need of treatment, i.e., a subject suffering from or at risk for a neurodegenerative disorder. The compounds can be administered to the subject using any convenient means capable of resulting in the desired effect, e.g., a decrease in microglial cell activation and/or cytokine secretion.

The compound can be incorporated into a variety of formulations for therapeutic administration. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, transdermal patches, suppositories, injections, inhalants and aerosols.

As such, administration of the compounds can be achieved in various ways, including oral, buccal, rectal, parenteral, intraperitoneal, intradermal, transdermal, pulmonary, intratracheal, etc., administration.

In pharmaceutical dosage forms, the compounds can be administered in the form of their pharmaceutically acceptable salts, or they can also be used alone or in appropriate association, as well as in combination, with other pharmaceutically active compounds. The following methods and excipients are merely exemplary and are in no way limiting.

For oral preparations, the compounds can be used alone or in combination with appropriate additives to make tablets, powders, granules or capsules. Examples of additives are conventional additives, such as lactose, mannitol, corn starch or potato starch; binders, such as crystalline cellulose, cellulose derivatives, acacia, corn starch or gelatins; disintegrators, such as corn starch, potato starch or sodium carboxymethylcellulose; lubricants, such as talc or magnesium stearate; and if desired, diluents, buffering agents, moistening agents, preservatives and flavoring agents.

The compounds of the invention can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol. If desired, conventional additives such as solubilizers, isotonic agents, suspending agents; emulsifying agents, stabilizers and preservatives may also be added. The concentration of therapeutically active compound in the formulation may vary from about 0.5–100 wt. %.

The compounds can be utilized in aerosol formulation to be administered via inhalation. The compounds of the present invention can be formulated into pressurized acceptable propellants such as dichlorodifluoromethane, propane, nitrogen and the like. Additionally, the compounds can be aerosolized in either liquid form or as a dry powder.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit (e.g., a teaspoonful, tablespoonful, tablet or suppository) contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Compounds for use in the method of the invention may also be small organic compounds having a molecular weight of more than 50 and less than about 2,500 daltons. Candidate compounds comprise functional groups necessary for structural interaction with proteins, particularly hydrogen bonding, and typically include at least an amine, carbonyl, hydroxyl or carboxyl group, preferably at least two of the functional chemical groups. The candidate compounds often comprise cyclical carbon or heterocyclic structures and/or aromatic or polyaromatic structures substituted with one or more of the above functional groups. Candidate compounds are also found among biomolecules including, but not limited to: peptides, saccharides, fatty acids, steroids, purines, pyrimidines, derivatives, structural analogs or combinations thereof.

The compounds are added to a host in a physiologically acceptable carrier, at a dosage from 5 mg to 1400 mg, more usually from 100 mg to 1000 mg, preferably 500 to 700 for a dose of 0.5 to 20 mg/kg weight. The dosage for compounds suppressing cholesterol biosynthesis is elected so that the cholesterol biosynthesis is reduced by 10 to 80%, more preferably 20 to 70% and even more preferably 25 to 50%. The dosage for compounds inhibiting the activity of $PGE_2$ receptors is elected so that the cytokine and/or cytotoxin secretion is reduced by about 20 to 100%, preferably 40 to 60%. The dosage for compounds inhibiting $PGE_2$ activity is elected so that the percentage of activity of the target molecule is reduced to a suitable level, e.g., microglial secretion is reduced by at least 50%.

The subject compositions will generally be administered daily, in an amount to provide at least about a 10 to 80%, more preferably 20 to 70%, even more preferably 25 to 50% decrease in the $A\beta:PGE_2$-induced release of cytokines. Generally, the total daily dosage will be at least about 10 mg, usually at least about 400 mg to 500 mg, preferably about 700 mg, and not more than about 1500 mg, usually not more than about 1000 mg. The amount may vary with the general health of the patient, the response of the patient to the drug, whether the $PGE_2$ antagonist is used by itself or in combination with other drugs, and the like. Daily administrations may be one or more times, usually not more than about four times, particularly depending upon the level of drug which is administered.

EXAMPLES

The following examples are put forth so as to provide those of ordinary skill in the art with a complete disclosure and description of how to make and use the subject invention, and are not intended to limit the scope of what is regarded as the invention nor are they intended to represent or imply that the experiments shown are all or the only experiments performed. Efforts have been made to ensure accuracy with respect to the numbers used (e.g., amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Example 1
Preparation and Characterization of Primary Glia Cell Cultures

As co-culture with astrocytes is known to promote the resting state for cultured microglia, mixed primary glial cultures are a particularly suitable system in which to examine $PGE_2:A\beta$ synergy. Briefly, cortices from P3 wild type mice were dissected in $Ca^{2+}$ and $Mg^{2+}$ free HBSS (Gibco). Meninges were carefully dissected away, and the tissue transferred to a dish containing HBSS supplemented with 0.53 mM EDTA and 0.05% trypsin. The tissue was incubated for 18 minutes at room temperature with occasional gentle agitation. Trypsin was removed and the tissue washed with HBSS twice prior to titration in growth medium consisting of high glucose DMEM supplemented with 10% fetal bovine serum (FBS), 110 mg/L sodium pyruvate, and 5 units/ml penicillin/streptomycin. The cell suspension was plated at 9 cortices in growth medium into one T75 and one T25 flask. The next day, nonadherent cells were removed. The culture was refed with growth medium at this time and once every 3 days following. When the culture appeared quite confluent, approximately one week, it was trypsinized and split into 48 well plates at $10^5$ cells/well. Experiments were initiated in several days when cells again reached confluence.

To characterize the mixed glial cultures, cell type specific markers were employed for immunocytochemistry. Staining was performed on cultures with 1) no treatment, i.e. media only; 2) treatment with 100 ng/ml LPS (48, hour exposure), or 3) treatment with 25 $\mu$M A$\beta$ prepared by the HFIP method and aged for 24 hours, (48 hour exposure). For immunocytochemistry, cultures were fixed with 4% paraformaldehyde in PBS for 30 minutes at 4° C. and washed with PBS containing 0.1% saponin. Endogenous peroxide activity was eliminated by incubation with $H_2O_2$ prior to preincubation with PBS containing 5% nonfat dry milk (PBS/NFDM). Incubation with primary antibody was performed overnight at 4° C. in PBS/NFDM. Antibody was visualized using Vectastain ABC kit according to manufacturer's recommendations and development with Vectastain DAB.

Anti-GFAP (Sigma) highlighted a lawn of astrocytes. Morphology of the astrocytes appeared typical when grown in medium alone but appeared somewhat reminiscent of activated astrocytes after LPS treatment and were notably activated following exposure to 24 hour aged A$\beta$. The presence of microglia was confirmed by immunocytochemistry with an anti-Mac-1 monoclonal antibody, mAB 5.1. After mAB 5.1 immunocytochemistry, microglia with a typical ramified, resting morphology were observed in the sample treated with media alone. Staining became slightly more intense following LPS or A$\beta$ treatment and some ameboid microglia could be seen, but the vast majority of microglia retained ramified profiles.

A number of compounds were tested to identify markers specific for activated microglia. Since the integrins LFA1 and VLA-4 were reported to fulfill this profile (e.g., Hailer et al., Glia 18:319–331, 1996), these molecules were tested using the system of the invention. Monoclonal antibodies to mouse CD11a (LFA1) and mouse CD49d (VLA-4) were obtained from Serotec. Both of these antibodies gave a very clean background and cultures grown in medium alone were devoid of any reaction product. In contrast, microglia in LPS treated cultures produced a strong signal with antibodies to both integrins. Microglia exposed to 24 hour aged A$\beta$ were filled even more densely with reaction product for both antibodies.

The high selectivity and clean background of these two markers suggest that they would be amenable to a quantitative assay, for example, by using fluorescent tagged antibodies and fluorimetry. To investigate cytokine secretion by activated microglia in the mixed cortical glial cultures, we measured intracellular and secreted IL-1$\alpha$ and secreted TNF-$\alpha$ levels following 48 hour exposure to various doses of LPS. The potency of LPS was similar for the three markers. In addition, the dose response curves are comparable to those obtained for LPS treatment of organotypic hippocampal slice cultures and the ratio of intracellular to secreted $IL1_\alpha$ is the same as seen for hippocampal slice and BV-2 mouse microglial cells.

Example 2
A$\beta$:$PGE_2$ Synergy Experiments in Primary Mixed Glial Cells

Endogenous $PGE_2$ levels and the ability of indomethacin to suppress $PGE_2$ were investigated by assaying medium conditioned by mature (confluent) primary mixed murine glial cultures in 48 well plates for 48 hours. Under basal conditions, $PGE_2$ was observed at just under 200 pg/ml conditioned media, in keeping with literature reports for primary cultures. Exposure to 100 ng/ml LPS dramatically increased this level to a concentration that saturated the assay at medium dilutions used, demonstrating the ability of the cultures to respond robustly to stimulus. Treatment of the cultures during the conditioning period with 14 µM indomethacin suppressed $PGE_2$ secretion to about 30 pg/ml in 48 hours. This is within the range in which would allow $PGE_2$:A$\beta$ synergy to be observed.

The effect of A$\beta$ in the presence and absence of exogenous $PGE_2$ was investigated in these primary cortical mixed glial cultures. An A$\beta$ peptide was resuspended at 4 mg/ml in 50% HFIP, incubated overnight at 37° C., dried in a Speed Vac, and resuspended in water at 4 mg/ml. The peptide was then "aged" at 37° C. for 11 or 24 hours and sonicated for 30 seconds on ice prior to use.

The aged A$\beta$ peptide was applied alone or in combination with exogenous 100 pg/ml $PGE_2$ to duplicate wells of cells that had been pretreated for 24 hours with 14 µM indomethacin. 100 pg/ml of $PGE_2$ is a low dose that is not expected to stimulate receptors for thromboxane or other prostenoids and is likely to be physiologically relevant. The indomethacin pretreatment was initiated at 3 days following seeding into wells and the 48 hour experimental treatments were initiated 4 days post seeding. Treatments were made in duplicate. After 48 hours, media and lysates were harvested and assayed.

Figure 2:
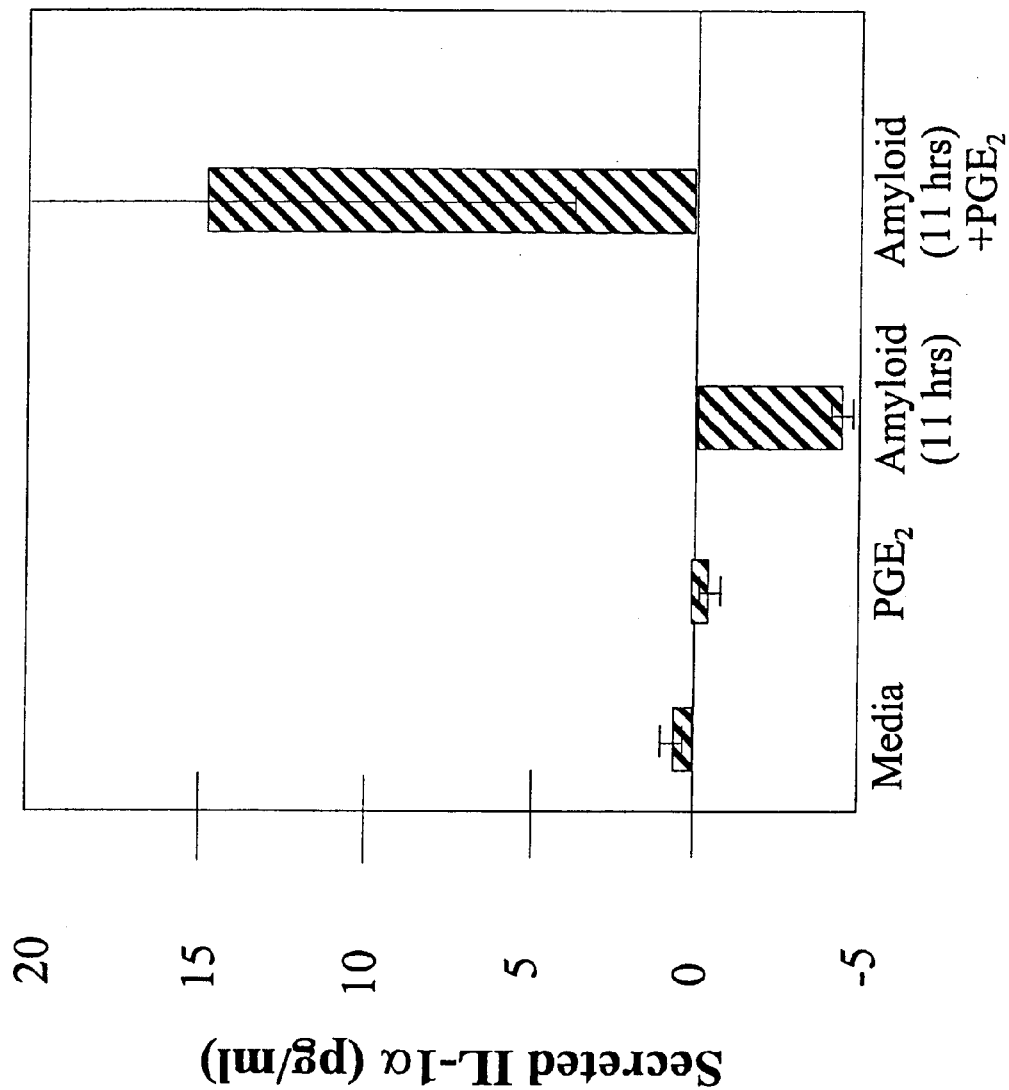
FIG. 2 is a bar graph illustrating the $PGE_2$:Aβ synergy in primary cortical mixed glial cells as evidenced by change in levels of secreted IL-1α.
Figure 3:
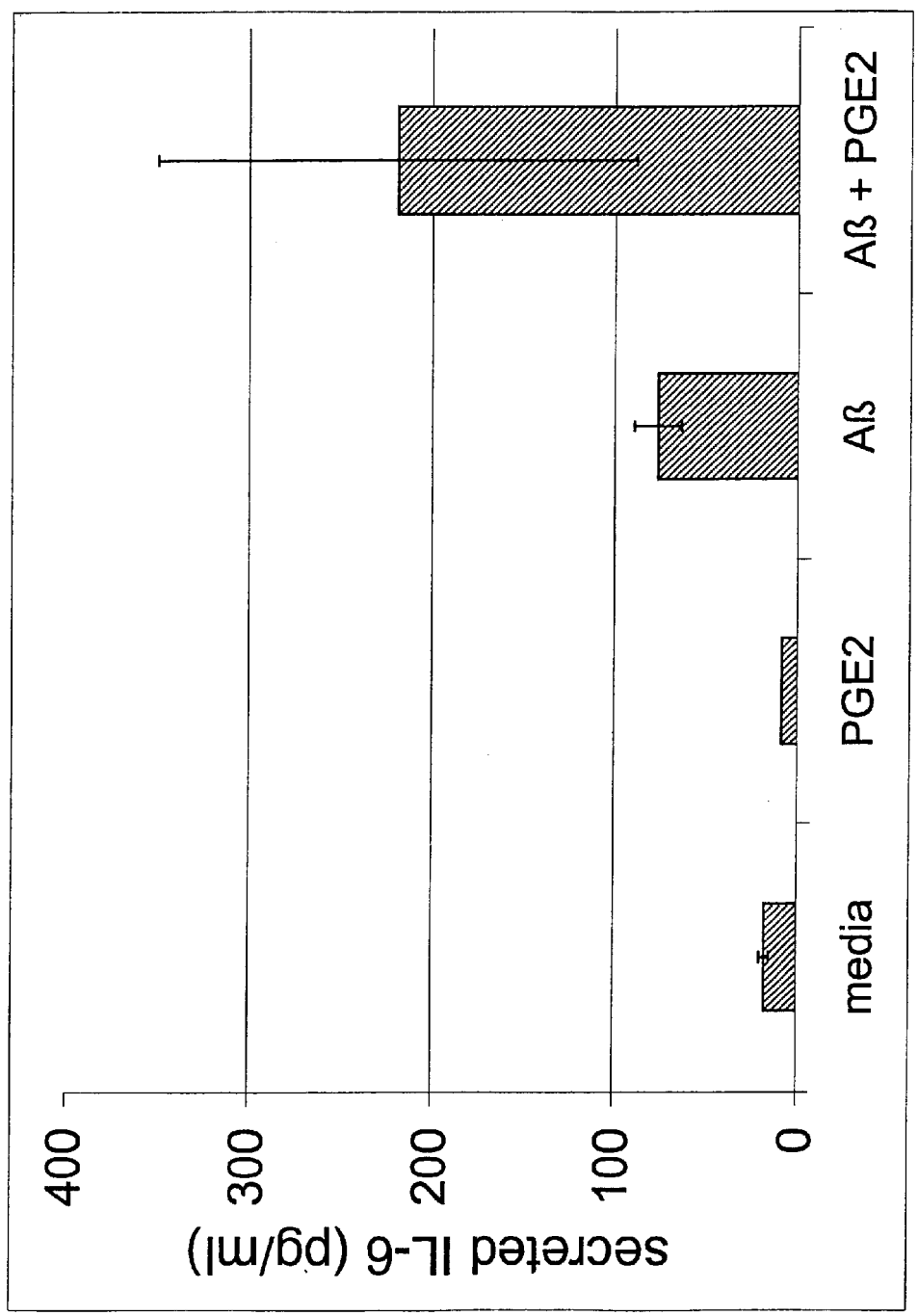
FIG. 3 is a bar graph illustrating the $PGE_2$:Aβ synergy in primary cortical mixed glial cells as evidenced by change in levels of secreted IL-6.

Neither $PGE_2$ nor 11 hour aged A$\beta$ alone had an effect on intracellular IL-1$\alpha$ (FIG. 1), a secreted IL-1$\alpha$ (FIG. 2) or secreted IL-6 (FIG. 3). However, the 11 hour aged A$\beta$ peptide exhibited a very striking synergy with $PGE_2$ for both cell-associated and secreted IL-1$\alpha$ induction. The IL-1$\alpha$ induction was more than 17 fold over the 11 hour aged A$\beta$ alone (even greater fold over $PGE_2$ alone) for cell associated cytokine and represented an induction of secreted cytokine from an undetectable level. We confirmed the cellular source of the if biochemical signal by immunocytochemistry with an anti-mouse IL-1$\alpha$ monoclonal antibody (R&D Systems).

Example 3

A$\beta$:$PGE_2$ Synergy Experiments in MMGT-16 Mouse Microglial Cell Culture

The protocol described above in Example 2 was then used to examine the synergy between $PGE_2$ and A$\beta$ in the mouse microglial cell line MMGT-16.

Figure 4:
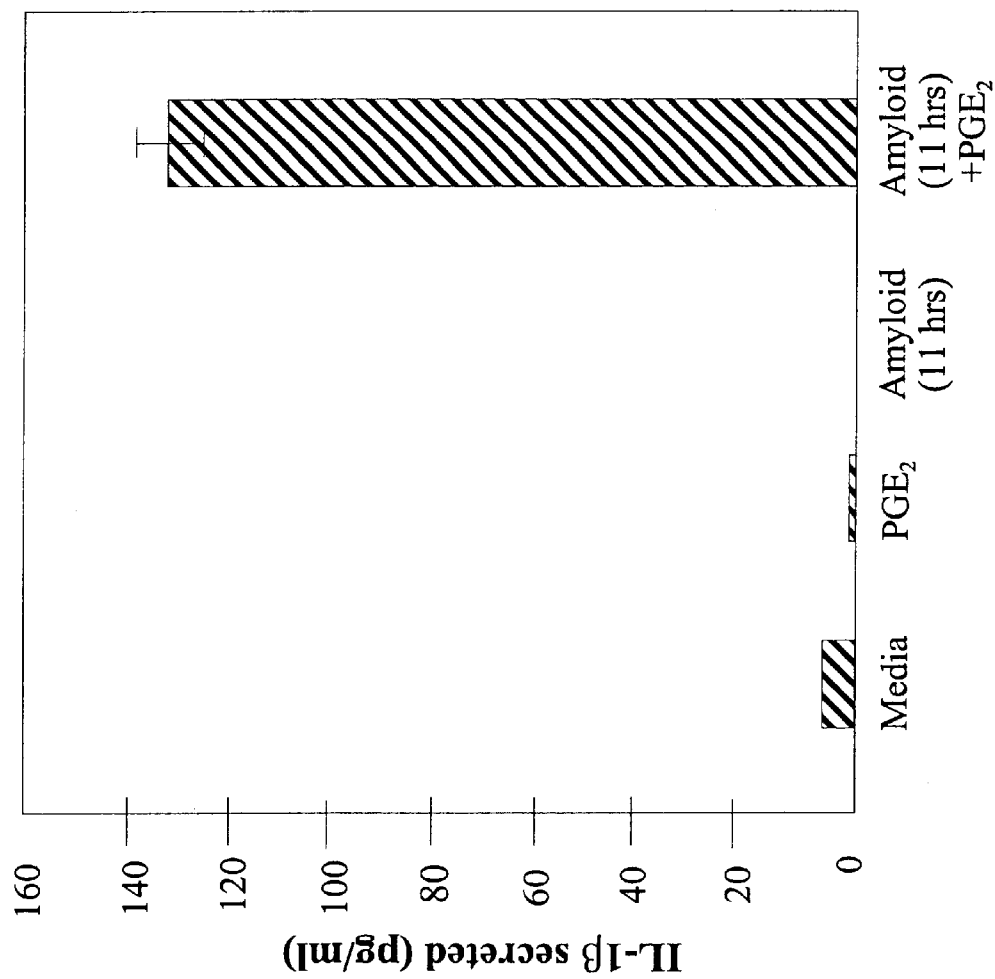
FIG. 4 is a bar graph illustrating the $PGE_2$:Aβ synergy in the mouse cell line MMGT-16 as evidenced by change in levels of secreted IL-1β.
Figure 5:
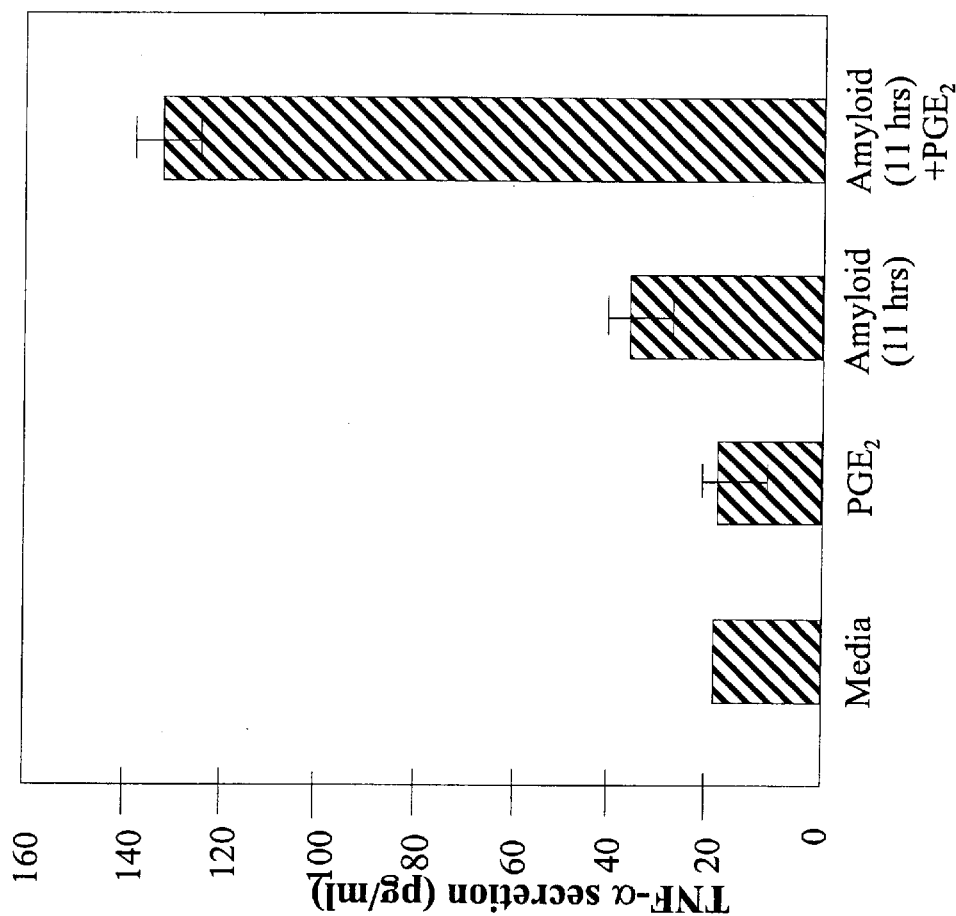
FIG. 5 is a bar graph illustrating the $PGE_2$:Aβ synergy in the mouse cell line MMGT-16 as evidenced by change in levels of secreted TNF-α.

Synergy in MMGT-16 cells was examined by measuring secretion of both TNF-$\alpha$ (FIG. 5) and IL-1$\beta$ (FIG. 4). The secretion of IL-1$\beta$ was unaffected by the addition of either $PGE_2$ or A$\beta$ alone, while addition of both resulted in a dramatic increase in the secretion of IL-1$\beta$. $PGE_2$ had no discernable effect on TNF-$\alpha$ secretion as well, while A$\beta$ alone had a modest affect on TNF-$\alpha$ secretion. The addition of both A$\beta$ and TNF-$\alpha$ together, however, resulted in a synergistic increase in the secretion of TNF-$\alpha$.

Example 4

A$\beta$:$PGE_2$ Synergy Experiments in MMGT-16 Mouse Microglial Cell Culture

BV-2 murine microglial cells display many phenotypic properties of primary microglia (Blasi et al., 1990; Bocchini et al., 1992), including responsiveness to A$\beta$ (Murphy et al., 1998). BV-2 cells are quasi-activated under basal culture conditions and secrete significant quantities of $PGE_2$, and A$\beta$ treatment alone induces IL-1$\alpha$ in BV-2 cells. A$\beta$-induced IL-1$\alpha$ elevation was not further enhanced by exogenous $PGE_2$ co-incubation. This was believed to result from co-activation by endogenous $PGE_2$.

The $PGE_2$ concentration in the 24 hour conditioned media from a BV-2 cell culture was a typically 500–800 pg/ml, well above that used for A$\beta$:$PGE_2$ stimulation. Endogenous $PGE_2$ in BV-2 cells could not be fully suppressed by indomethacin. Overnight pretreatment with 14 µM indomethacin, followed by a 24 hour conditioning period in the continued presence of the mixed COX 1/COX 2 inhibitor, resulted in $PGE_2$ levels ranging from 30 to 200 pg/ml. Higher doses of indomethacin were toxic to the BV-2 cells, and a survey of additional COX inhibitors alone and in combination did not yield a more effective treatment. A$\beta$ activation of BV-2 cells is highly reproducible, having been observed in 90% of experiments with a mean stimulation of 3.2 fold (n=21; p<0.05 vs. media control).

Example 5

A$\beta$:$PGE_2$ Synergy Experiments in Human Fetal Mixed Glial Cells

The modified protocol of the experiment from Example 2 was then performed to examine the synergy of A$\beta$ and $PGE_2$ in human fetal mixed glial cultures. Tissue was obtained from Advanced Bioscience Resource, a non-profit group that supplies live tissue to researchers in the San Francisco Bay Area. Cultures from 10 cortices were split from the two T75 flask of original plating into two T150 flasks and then into 48 well plates. Both splits, as well as initiation of the experimental treatments, were performed following 24 hours at full confluency. The cell type composition ratio of the human preparation appears very similar to the preparation used in Example 1 by phase contrast microscopy. A$\beta$ peptide treatments are performed at 26 g, and an 11 hour A$\beta$ aging time point was used.

Example 6

EP Receptor Analysis

First, EP receptor subtypes present on microglia were determined. RT-PCR of BV-2 microglial RNA revealed that EP1, EP2, and EP4 mRNAs are made by microglia, but that EP3 is absent. Since BV-2 and MMGT-16 cell lines express EP1, EP2, and EP4 $PGE_2$ receptor isoforms, these receptors were candidates for mediating the A$\beta$:$PGE_2$ synergistic-effect. EP3 was not detected, ruling out this pharmacologically untenable target as mediating the effect of interest. All isoforms were observed in whole murine brain. The isoforms of the $PGE_2$ present on human microglia was determined to investigate the potential AD relevance of the identified A$\beta$-$PGE_2$ synergistic effect. RNA was obtained from microglial cultures prepared from human fetal brain, and cell lysates were obtained from microglial cultures prepared from AD and non-demented (ND) elderly subjects. Minimally sufficient material to make the desired determinations was available from the AD and ND cultures. Several primer pairs for each receptor isoform were designed using database sequences. These pairs are shown below:

|  | 3' Primer | 5' Primer |
| --- | --- | --- |
| EP1 primers | GCAGCGAGCTGGCCTCCCAGG<br>SEQ ID NO: 1 | CCAGCTTGTCGGTATCATGGTGG<br>SEQ ID NO: 2 |
| EP2 primers | GTTGCATCTTGTGTTCTTAATG<br>SEQ ID NO: 3 | GCTTCTCATTGTCTCGGTGCTCG<br>SEQ ID NO: 4 |
| EP3 primers | CAACTGATGTCTGATTGAAGATC<br>SEQ ID NO: 5 | GGAGACCAGCAGACCGACAGCAC<br>SEQ ID NO: 6 |
| EP4 primers | GCAATAGAGAAGATCAAATGC<br>SEQ ID NO: 7 | CTGATAAGTTCAGTGTTTCAC<br>SEQ ID NO: 8 |

Since mouse kidney expresses is known to all receptor subtype mRNA species, total human kidney RNA was used as a positive control to determine optimal RT-PCR conditions and to select the best primer sets.

Following optimization of the PCR protocol, cDNA was prepared from fetal-derived microglial RNA in the presence or absence of reverse transcriptase. When the RNA was shown to be contaminated by DNA by positive PCR bands obtained with material lacking reverse transcriptase, a second reverse transcription reaction was performed following DNase treatment of the RNA. RT-PCR revealed the presence of EP1, EP2, and EP4. $PGE_2$ receptor isoform mRNA but not of EP3 mRNA in the fetal microglial material (Table 1).

|  | AD28<br>μglia | AD21<br>μglia | ND31<br>μglia | ND24<br>μglia | Fetal<br>μglia | Brain | Kidney |
| --- | --- | --- | --- | --- | --- | --- | --- |
| APP695 | nd | nd | ++ | nd | ++ | ++ | ++ |
| APP751 | nd | nd | ++ | nd | ++ | +/− | ++ |
| EP1 | + | + | + | + | + | ++ | ++ |
| EP2 | + | +/− | + | +/− | + | ++ | + |
| EP3 | − | −* | − | − | − | +++ | +++ |
| EP4 | +++ | +++ | +++ | +++ | +++ | +++ | +++ |
| DP | − | ++ | − | + | ++ | ++ | ++ |

(Nd) not done;
(−) absent;
(+/−) faint;
(+) clearly detectable;
(++) strong;
(+++) very strong
AD28: 84 year old AD; 17 d.i.v.
ND31: 79 year old non-demented; 28 d.i.v.
AD21: 96 year old AD; 51 d.i.v.
ND24: 83 year old non-demented; 60 d.i.v.
Fetal: ~22 weeks gestation; ~14 d.i.v.

Next, the protocol was repeated twice using matched pairs of AD and ND cell lysate samples. Sufficient material was available for only a single determination, so after RNA was isolated it was DNAse treated prior to cDNA preparation. For both sets of samples, once again RT PCR revealed the presence of EP1, EP2, and EP4 $PGE_2$ receptor isoform mRNA and the absence of EP3 mRNA. β-APP RT-PCR was performed on some samples to confirm the presence of sufficiently high quality mRNA, with satisfactory results. DP RT-PCR was performed since $PGE_2$ is present in brain and is secreted by stimulated microglial cultures. The presence of mRNA for the $PGE_2$ receptor was detected in most samples. All $PGE_2$ receptor isoforms, as well as DP, were detected in RNA prepared from whole human brain. In all cases, the PCR product which scored positive for a prostaglandin receptor was a band of the predicted size that hybridized to an oligonucleotide probe internal to the predicted fragment. Overall, results with primary human cultured microglia agree well with those from murine immortalized microglial cell lines.

Similar experiments using primers designed and optimized for the murine EP sequences were performed to detect $PGE_2$ isoforms in mouse microglia. BV-2 and MMGT-16 murine microglia were shown to contain EP1, EP2, and EP4 but not EP3 specific mRNA. Murine brain and mixed murine glial cultures contain mRNA for all four EP isoforms. The absence of EP3 eliminates this receptor as a potential mediator of the synergistic effect. In the mixed glial culture experiments, it cannot be deduced whether the EP1, EP3, or EP4 products are derived from microglia, from contaminating astrocytes or both.

While it must be emphasized that the current application of RT-PCR is nonquantitative, a few observations suggesting difference in abundance can be made. Qualified comparisons can be made within a given PCR reaction set, so that differences in efficiency of reaction conditions and primer sets are not an issue. For example, RT-PCR bands were equally strong for microglial and whole brain samples only in the case of EP4, EP1, and EP2 bands were weaker for all microglial samples than for whole brain, reflecting either differences in quantity of high quality template (cDNA was not strictly quantitated in the reactions) or true differences in abundance. We do not know if the EP4 reaction saturated at the same cycle number for different templates and cannot conclude equal abundance of EP4 in the different source. However, the data does suggest higher proportion of EP4 in microglia than whole brain relative to other isoforms.

Example 7

Involvement of EP2 and EP4 in Aβ:$PGE_2$ Activation

Two of the four $PGE_2$ isoforms, EP2 and EP4, are coupled to $G_s$ and elevate cAMP levels upon activation. EP3 is coupled to $G_i$ and inhibits cAMP production while EP1 increased $Ca^{++}_i$. As a first step in distinguishing the receptor isoform mediating the $PGE_2$ signal, the second messenger in the Aβ coactivation pathway was identified. The slowly hydrolyzable, cell permeant cAMP analog 8-Br-cAMP was shown to have the ability to substitute for $PGE_2$ as a coactivator with Aβ, strongly indicating the either EP2 or EP4 mediates the synergistic activation of microglia. Further evidence that the $PGE_2$ signaling pathway involves cAMP is the ability of the direct adenylate cyclase activator forskolin to substitute for $PGE_2$ as an Aβ co-activator, and of the type IV (cAMP specific) phosphodiesterase inhibitor rolipram to enhance Aβ:$PGE_2$ stimulation of microglial cytokine production.

Figure 6:
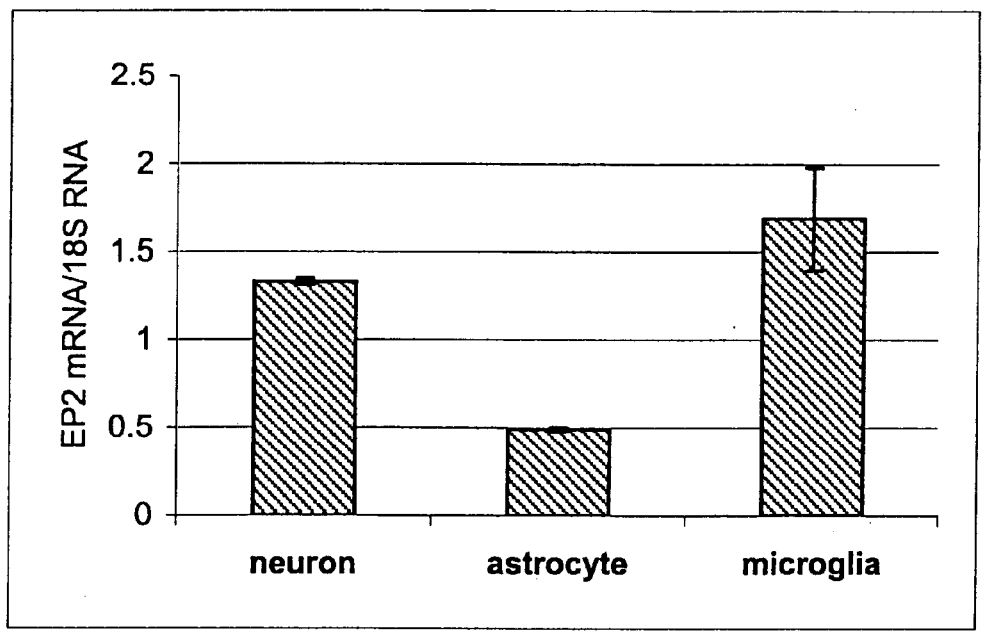
FIG. 6 is a set of bar graphs illustrating levels of mRNA for $PGE_2$ receptor isoforms EP2 and EP4 in microglia and astrocytes.
Figure 6:
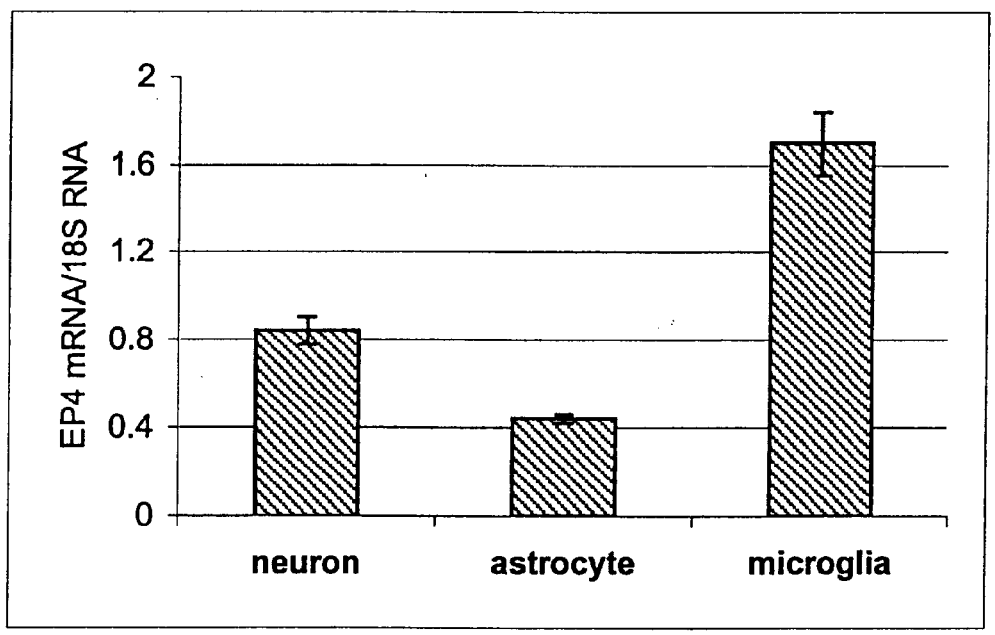

Based on the second messenger evidence that cAMP mediates the PGE2 signal component of Aβ:$PGE_2$ synergy, receptor isoforms EP2 and EP4 were examined more closely. The relative abundance of EP2 and EP4 mRNA on brain cell types was determined by a real time quantitative PCR assay using Taqman. Primary cultures of murine cortical neurons, astrocytes, and microglia were prepared as the source of RNA template. Microglia expressed three-fold higher levels of EP2 mRNA, and four fold higher levels of EP4 RNA than did astrocytes (FIG. 6). Since specific PCR reaction efficiencies can differ greatly, values from the EP2 assay cannot be compared to values for the EP4 assay.

To further determine the potential role of EP2 and EP4 in Aβ:PGE$_2$, the activity and/or expression of each was blocked. An EP1/2 selective antagonist AH6809 (Woodward et al., 1995) was used to block the activity of EP2. The activity of AH6809 was confirmed by [$^3$H]-PGE$_2$ binding and PGE$_2$ stimulated cAMP accumulation functional assays. The expected K$_i$ of 1 μM for AH6809 inhibition of [$^3$H]-PGE$_2$ binding to EP1, and EC$_{50}$ of 1 μM for inhibition of PGE$_2$ induced cAMP generation were confirmed. Selectivity of the compound was demonstrated by lack of AH6809 inhibition of [$^3$H]-PGE$_2$ binding to EP4.

Figure 7:
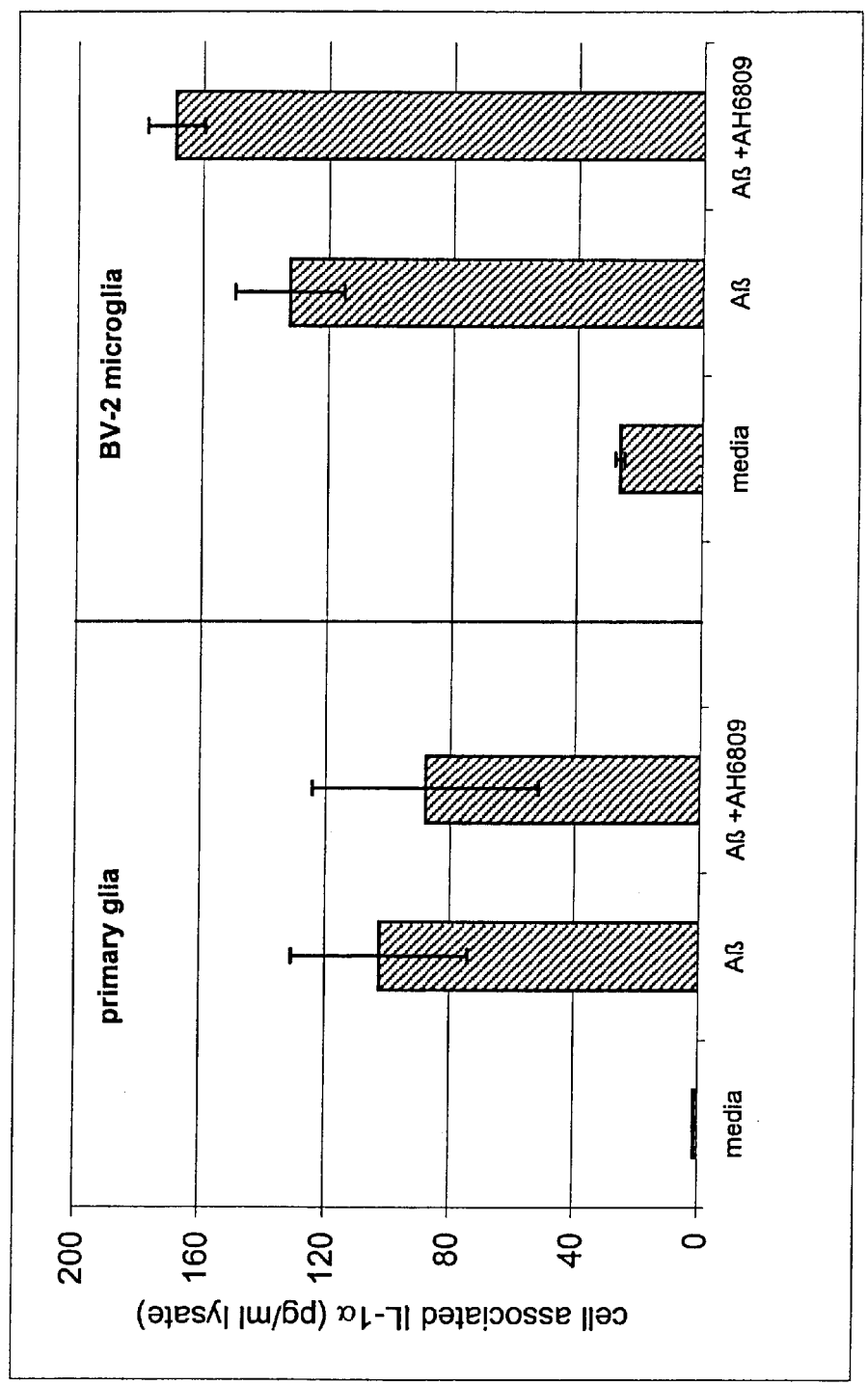
FIG. 7 is a bar graph illustrating levels of activation of primary glia and microglia in the presence of EP2 antagonist AH6809.

The EP2 antagonist AH6809 was found to have has no effect on Aβ:PGE$_2$ activation of primary glia, even at a 10-fold higher concentration than the K$_d$ (FIG. 7). In addition, the EP2 antagonist AH6809 had no effect on Aβ stimulation of BV-2 cells (FIG. 7). Aβ treatment of BV-2 microglia has two striking morphological effects. First, cells clumped in a manner consistent with the well documented microglial chemotactic activity to Aβ. Second, the morphology of individual cells is altered such that they change from a spherical to an elongated, process bearing shape. The EP2 antagonist had no effect on either response, indicating that EP2 does not play a role.

Since selective EP4 antagonists were unavailable, an antisense approach is used to probe involvement of EP4 in Aβ:PGE2 activation of microglia. The antisense oligonucleotides are first tested for their ability to inhibit EP4 expression by measuring their effect on PGE$_2$ stimulation of cAMP accumulation, an EP2/EP4 mediated event. Once the activity of the antisense oligonucleotide is confirmed, the effect of the oligonucleotide on Aβ:PGE$_2$ activation is tested in BV-2 microglial cells.

In cells treated for 48 hours with EP4 antisense oligonucleotides, accumulation of cAMP upon PGE$_2$ exposure was reduced ~50%. The residual cAMP stimulation could be due to residual EP4 expression or to EP2 receptor-mediated G$_s$ stimulation. Parallel experiments using fluorescently tagged oligonucleotides composed of the same sequence revealed penetration of essentially all cells by the oligonucleotides.

Figure 8:
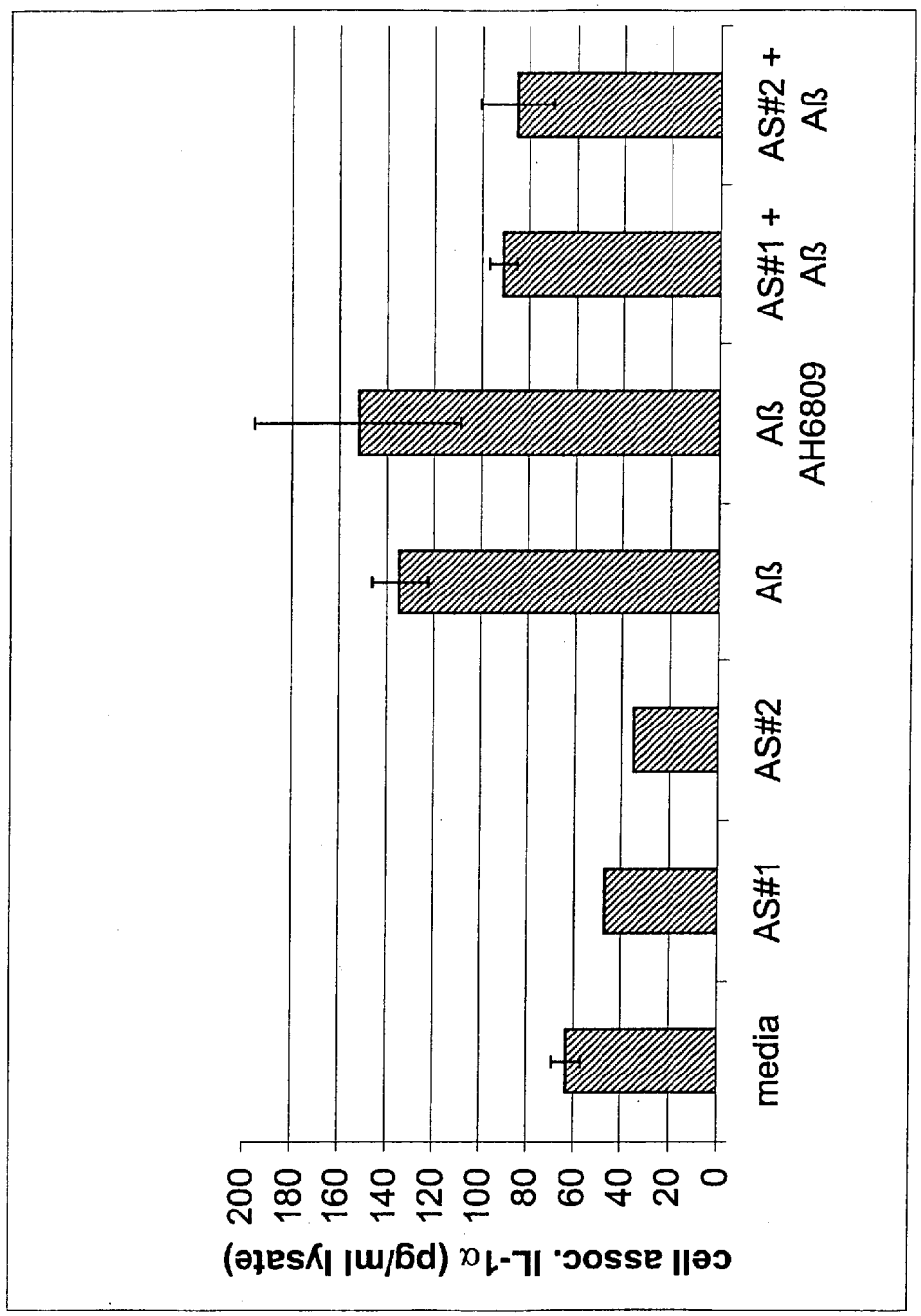
FIG. 8 is a bar graph illustrating the ability of EP4 antisense oligonucleotides to attenuate Aβ stimulation of IL-1α in BV-2 cells.

Next, BV-2 cells are pretreated with the antisense oligonucleotides for 48 hours and then, in the continued presence of the oligonucleotide, the pretreated cells are exposed to Aβ. The antisense EP4 construct decreases the morphological response to Aβ, exhibiting both decreasing clumping of the cells and fewer cells having the elongated, process bearing shape. A decreased response to Aβ treatment is confirmed by detection of lower levels of secretion of both TNF-α and IL-1β. The EP4 construct decreases IL-1β by 50%, a substantial effect for this method of inhibition (FIG. 8).

The instant invention is shown and described herein in what is considered to be the most practical and preferred embodiments. It is recognized, however, that departures may be made therefrom, which are within the scope of the invention, and that obvious modifications will occur to one skilled in the art upon reading this disclosure.

What is claimed is:

1. An assay comprising the acts of:
   providing cultured cells, the cultured cells comprising microglia cells;
   contacting the cultured cells with an amyloid β (Aβ) and a prostaglandin $E_2$ compound;
   contacting the cultured cells with a test compound;
   determining the effect of the test compound on the cultured cells' activation, wherein determining the effect of the compound on the cultured cells' activation is by measuring an alteration of an Aβ: Prostaglandin $E_2$ synergy effect of a prostaglandin $E_2$-mediated pathway; and comparing the alteration of an Aβ: Prostaglandin $E_2$ synergy effect to a measurement of the an Aβ: Prostaglandin $E_2$ synergy effect of a control culture, wherein the control culture is in contact with an amyloid β and a prostaglandin $E_2$ compound and not in contact with the test compound.

2. The assay of claim 1, wherein the alteration of the prostaglandin $E_2$-mediated pathway comprises changes in the expression of a cytokine.

3. The assay of claim 2, wherein the cytokine is selected from the group consisting of TNF-α, IL-1α and IL-6.

4. The assay of claim 1, wherein the effect on cultured cells' activation is determined by comparing the effect of the compound on the alteration of an Aβ: Prostaglandin $E_2$ synergy effect with a standardized profile of Aβ: Prostaglandin $E_2$ synergy effect of cultured cells' activity measurements.

5. The assay of claim 1, wherein the measuring an alteration of an Aβ: Prostaglandin $E_2$ synergy effect comprises;

measuring a level of expression of at least one cytokine of the cultured cells, the cytokine selected from the group of cytokines consisting of Interleukin-1α (IL-1α), Interleukin-1β (IL-1β), Interleukin-6 (IL-6), and Tumor Necrosis Factor-α (TNF-α).

6. The assay of claim 1, wherein the compound is a prostaglandin $E_2$ antagonist.

7. The assay of claim 1, wherein the alteration of an Aβ:Prostaglandin $E_2$ synergy effect of the prostaglandin $E_2$ pathway comprises the compound effecting the activity of a prostaglandin $E_2$ EP4 isoform.

8. The assay of claim 1, wherein said alteration of an Aβ:Prostaglandin $E_2$ synergy effect of the prostaglandin $E_2$ pathway comprises the compound inhibiting a prostaglandin $E_2$ receptor.

9. The assay of claim 1, wherein the cultured cells are a microglial cell line.

10. The assay of claim 9, wherein the cell line is a MMGT-16 or BV-2 murine cell line.

11. The assay of claim 1, wherein the cultured cells are a primary glial culture.

* * * * *